United States Patent [19]

Atkinson et al.

[11] 4,358,455
[45] Nov. 9, 1982

[54] ARALKYLAMINDETHANOL HETEROCYCLIC COMPOUNDS

[75] Inventors: Joseph G. Atkinson, Montreal, Canada; John J. Baldwin, Gwynedd Valley; David E. McClure, Lansdale, both of Pa.

[73] Assignee: Merck & Co., Inc., Rahway, N.J.

[21] Appl. No.: 219,725

[22] Filed: Dec. 23, 1980

[51] Int. Cl.$^3$ .................... A61K 31/44; C07D 211/86
[52] U.S. Cl. ................................. 424/263; 546/300; 546/312; 546/270
[58] Field of Search ..................... 546/300, 312, 270; 424/263

[56] References Cited

U.S. PATENT DOCUMENTS

| | | | |
|---|---|---|---|
| 3,644,353 | 2/1972 | Lunt et al. | 546/300 |
| 3,705,233 | 12/1972 | Lunt et al. | 546/300 |
| 3,952,101 | 4/1976 | Jen et al. | 546/300 |

Primary Examiner—John M. Ford
Assistant Examiner—Robert C. Whittenbaugh
Attorney, Agent, or Firm—Daniel T. Szura; Martin L. Katz; Rudolph J. Anderson, Jr.

[57] ABSTRACT

Heterocyclic aminoethanols of the formula $$\text{Het—CHOH—CH}_2\text{—NH—aralkyl}$$

where het is a 6–10 membered N heterocycle are disclosed. The compounds are useful as pharmaceuticals.

26 Claims, No Drawings

ARALKYLAMINDETHANOL HETEROCYCLIC COMPOUNDS

BACKGROUND OF THE INVENTION

The present invention is concerned with heterocyclic compounds of the formula Het-CHOH-CH$_2$-NH-aralkyl.

Substituted phenylaminoethanols of the formula Ph-CHOH-CH$_2$-NH-aralkyl where Ph is a substituted phenolic group are disclosed in U.S. Pat. Nos. 3,644,353; 3,705,233. These compounds have random activity as β-adrenergic stimulants and β-adrenergic blockers. These compounds are taught to be useful as pharmaceuticals for treating glaucoma and cardiovascular disorders such as hypertension and arrhythmias.

Heterocyclic aminoethanols which have pharmaceutical utility have been discovered.

SUMMARY OF THE INVENTION

Heterocyclic compounds of the formula Het-CHOH-CH$_2$-NH-aralkyl where Het is 6-10-membered N-heterocyclic and their use as pharmaceuticals.

DESCRIPTION OF THE PREFERRED EMBODIMENTS

An embodiment of the present invention is compounds of the formula

Het-R    I and pharmaceutically acceptable salts thereof where Het is

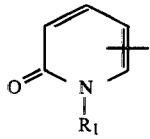 (a)

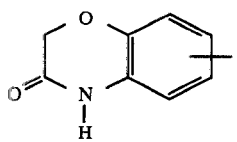 (b)

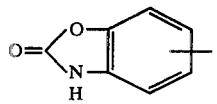 (c)

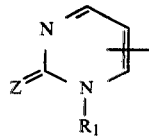 (d)

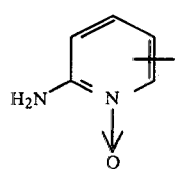 (e)

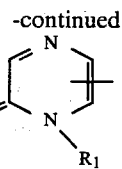 (f)

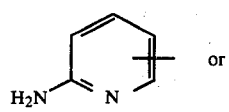 (g)

or

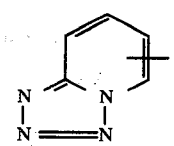 (h)

tautomers thereof, and pharmaceutically acceptable salts thereof wherein
R$_1$ is H or OH, Z is O or NH, $$R \text{ is } \overset{OH}{\underset{|}{CH}}-CH_2-NHR_3$$

wherein

R$_3$ is 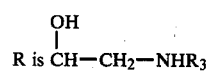

wherein
R$_4$ and R$_5$ are independently selected from H and C$_1$-C$_3$alkyl,
Y is CH$_2$, (CH$_2$)$_2$, (CH$_2$)$_3$, (CH$_2$)$_4$ or —CH$_2$O—
R$_6$ is H, OH, O—C$_1$-C$_3$alkyl, methylenedioxy halogen or C$_1$-C$_3$alkyl and
n is 1 or 2.

The pharmaceutically acceptable salts are the salts of the Formula I base with suitable organic or inorganic acids. Suitable organic acids include carboxylic acids such as acetic acid, pamoic acid, pivalic acid, oxalic acid, lauric acid, pelargonic acid, citric acid, tartaric acid, maleic acid, oleic acid, propanoic acid, succinic acid, isobutyric acid, malic acid and the like, the noncarboxylic acids such as isethionic acid and methane sulfonic acid. Maleic acid salts are preferred. Suitable inorganic acids are the hydrogen halides e.g. HCl, HI, HBr, phosphoric acid and sulfuric acid. The hydrohalide salts, and especially the hydrochlorides, are preferred. These salts can be prepared by treating the free base with an appropriate amount of a suitable acid, generally in a solvent.

R$_3$ is the phenalkyl group

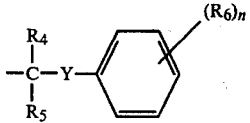 (e)

Each of R$_4$ and R$_5$ may be C$_1$-C$_3$alkyl e.g. CH$_3$, C$_3$H$_7$, C$_2$H$_5$ and the like or hydrogen. CH$_3$ and H are preferred R$_4$/R$_5$ substituents while it is more preferred when one or both of R$_4$/$_5$ is CH$_3$. Y is CH$_2$O, CH$_2$ or (CH$_2$)$_{1-4}$, with $CH_2$ and $(CH_2)_2$ being preferred. $R_6$ is H, OH, O-$C_1$-$C_3$alkyl, halogen (Br, Cl, I or F with Br and Cl being preferred), methylenedioxy or $C_1$-$C_3$-alkyl, branched or linear. H and $OCH_3$ are preferred definitions of $R_6$. Examples illustrating useful $R_3$ groups are

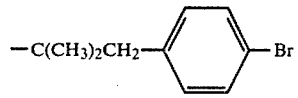

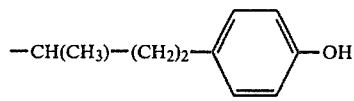

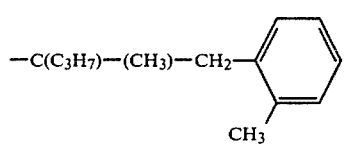

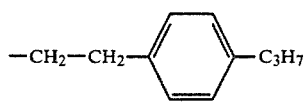

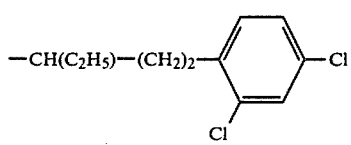

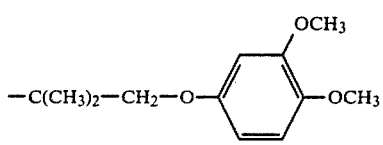

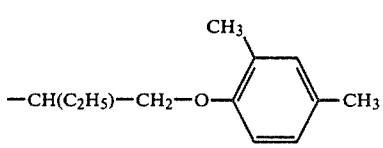

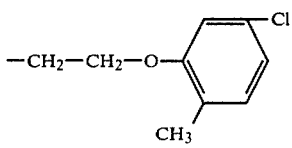

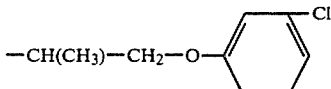

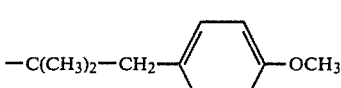

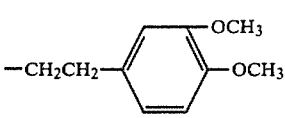

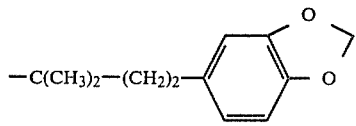

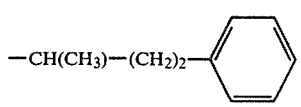

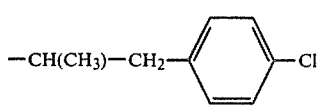

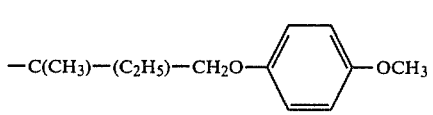

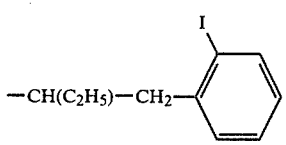

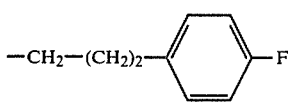

and the like.

Of the heterocyclic groups, the (a), (b), (c), (e), (g) and (h) groups are preferred; the (a), (b), (c), (e) and (g) groups are more preferred; the (a), (b), (e) and (g) groups are especially preferred. The (b), (e) or (g) groups are more particularly preferred.

The monocyclic group

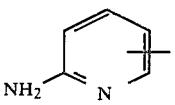

and the bicyclic group

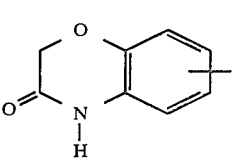

are most preferred. In the heterocyclic groups tautomers occur and are included. An illustrative example of such tautomers is

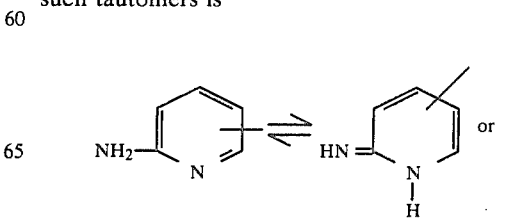

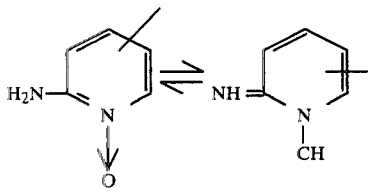

The compounds of formula I have one chiral center at the 1-position in the aminoethanol substituent and can have a second chiral center when the $R_4$ and $R_5$ substituents in the $R_3$ group are different. The chiral centers confer optical activity on the formula I compounds.

All the optical isomer forms, that is mixtures of enantiomers or diastereomers, e.g. racemates as well as individual enantiomers or diasteriomers of formula I are included. These individual enantiomers are commonly designated according to the optical rotation they effect by the symbols (+) and (−), (L) and (D), (l) and (d) or combinations thereof. These isomers may also be designated according to their absolute spatial configuration by (S) and (R), which stands for sinister and rectus, respectively.

The individual optical isomers may be prepared using conventional resolution procedures, e.g., treatment with an appropriate optically active acid, separating the diasteriomers and then recovering the desired isomer.

A compound of Formula I is useful for treating glaucoma since it deceases intraocular pressure when topically administered to the eye. The ability to lower intraocular pressure is determined using an in-vivo protocol in a rabbit model.

Said compound is preferably administered in the form of an opthalmic pharmaceutical composition adapted for topical administration to the eye such as a solution, an ointment or as a solid insert. Formulations of the compound may contain from 0.01 to 5% and especially 0.5 to 2% of medicament. Higher dosages as, for example, about 10% or lower dosages can be employed provided the dose is effective in lowering intraocular pressure. As a unit dosage form, between 0.001 to 5.0 mg., preferably 0.005 to 2.0 mg., and especially 0.005 to 1.0 mg of the compound is generally applied to the human eye.

The pharmaceutical composition which contains the compound may be conveniently admixed with a non-toxic pharmaceutical organic carrier, or with a non-toxic pharmaceutical inorganic carrier. Typical of pharmaceutically acceptable carriers are, for example, water, mixtures of water and water-miscible solvents such as lower alkanols or aralkanols; vegetable oils; polyalkylene glycols; petroleum based jelly; ethyl cellulose; ethyl oleate; carboxymethylcellulose; polyvinylpyrrolidone; isopropyl myristate, and other conventionally employed acceptable carriers. The pharmaceutical preparation may also contain non-toxic auxiliary substances such as emulsifying, preserving, wetting agents, bodying agents and the like, as for example, polyethylene glycols 200, 300, 400 and 600, carbowaxes 1,000, 1,500, 4,000, 6,000 and 10,000 bacterial components such as quaternary ammonium compounds, phenylmercuric salts known to have cold sterilizing properties and which are non-injurious in use, thimerosal, methyl and propyl paraben, benzyl alcohol, phenyl ethanol, buffering ingredients such as sodium chloride, sodium borate, sodium acetate, glyconate buffers, and other conventional ingredients such as sorbitan monolaurate, triethanolamine, oleate, polyoxyethylene sorbitan monopalmitylate, dioctyl sodium sulfosuccinate, monothioglycerol, thiosorbitol, ethylenediamine tetracetic acid, and the like. Additionally, suitable ophthalmic vehicles can be used as carrier media for the present purpose including conventional phosphate buffer vehicle systems, isotonic boric acid vehicles, isotonic sodium chloride vehicles, isotonic sodium borate vehicles and the like. The pharmaceutical preparation may also be in the form of a solid insert. For example, one may use a solid water soluble polymer as the carrier for the medicament. The polymer used to form the insert may be any water soluble non-toxic polymer, for example, cellulose derivatives such as methylcellulose, sodium carboxymethyl cellulose, (hydroxyloweralkyl cellulose), hydroxyethyl cellulose, hydroxypropyl cellulose, hydroxypropylmethyl cellulose; acrylates and as polyacrylic acid salts; natural products such as gelatin, alginates, pectins, tragacanth, karaya, chondrus, agar, acacid; the starch derivatives such as starch acetate, hydroxyethyl starch ethers, hydroxypropyl starch, as well as other synthetic derivatives such as poly vinyl alcohol, polyvinyl pyrrolidone, polyvinyl methyl ether, polyethylene oxide, neutralized carbopol and xanthan gum, and mixtures of said polymer.

Preferably the solid insert is prepared from cellulose derivatives such as methylcellulose, hydroxyethyl cellulose, hydroxypropyl cellulose or hydroxypropylmethyl cellulose or from other synthetic materials such as polyvinyl alcohol, polyvinyl pyrrolidone, polyethylene oxide or polyvinyl methylether. Hydroxypropyl cellulose, one of the preferred polymers for the preparation of the insert is available in several polymeric forms, all of which are suitable in the preparation of these inserts. Thus, the product sold by Hercules, Inc. of Wilmington, Del. under the name KLUCEL such as KLUCEL HF, HWF, MF, GF, JF, LF and EF which are intended for food or pharmaceutical use are particularly useful. The molecular weight of these polymers useful for the purposes described herein may be at least 30,000 to about 1,000,000 or more. Similarly, an ethylene oxide polymer having a molecular weight of up to 5,000,000 or greater, and preferably 100,000 to 5,000,000 can be employed. Further, for example, POLYOX a polymer supplied by Union Carbide Co. may be used having a molecular weight of about 50,000 to 5,000,000 or more and preferably 3,000,000 to 4,000,000. Other specific polymers which are useful are polyvinyl pyrrolidine having a molecular weight of from about 10,000 to about 1,000,000 or more, preferably up to about 350,000 and especially about 20,000 to 60,000; polyvinyl alcohol having a molecular weight of from about 30,000 to 1,000,000 or more particularly about 400,000 and especially from about 100,000 to about 200,000; hydroxypropylmethyl cellulose having a molecular weight of from about 10,000 to 1,000,000 or more, particularly up to about 200,000 and especially about 80,000 to about 125,000; methyl cellulose having a molecular weight of from about 10,000 to about 1,000,000 or more, preferably up to about 200,000 and especially about 50 to 100,000; and CARBOPOL (carboxyvinyl polymer) of B. F. Goodrich and Co. designated as grades 934, 940 and 941. It is clear that for the purpose of this invention the type and molecular weight of the polymer is not critical. Any water soluble polymers can be used having an average molecular weight which will afford dissolution of the polymer and accordingly the medicament in any desired length of time. The inserts, therefore, can be prepared to allow for retention and accordingly effectiveness in the eye for any desired period. The insert can be in the form of a square, rectangle, oval, circle, doughnut, semi-circle, ¼ moon shape, and the like. Preferably the insert is in the form of a rod, doughnut, oval or ¼ moon. The insert can be readily prepared, for example, by dissolving the medicament and the polymer in a suitable solvent and the solution evaporated to afford a thin film of the polymer which can then be subdivided to prepare inserts of appropriate size. Alternatively the insert can be prepared by warming the polymer and the medicament and the resulting mixture molded to form a thin film. Preferably, the inserts are prepared by molding or extrusion procedures well known in the art. The molded or extruded product can then be subdivided to afford inserts of suitable size for administration in the eye.

The insert can be of any suitable size to readily fit into the eye. For example, castings or compression molded films having a thickness of about 0.25 mm. to 15.0 mm. can be subdivided to obtain suitable inserts. Rectangular segments of the cast or compressed film having a thickness between about 0.5 and 1.5 mm can be cut to afford shapes such as rectangular plates of 4×5-20 mm or ovals of comparable size. Similarly, extruded rods having a diameter between about 0.5 and 1.5 mm. can be cut into suitable sections to provide the desired amount of polymer. For example, rods of 1.0 to 1.5 mm. in diameter and about 20 mm. long are found to be satisfactory. The inserts may also be directly formed by injection molding. It is preferred that the ophthalmic inserts containing the medicament of the present invention be formed so that they are smooth and do not have any sharp edges or corners which could cause damage to the eye. Since the terms smooth and sharp edges or corners are subjective terms, in this application these terms are used to indicate that excessive irritation of the eye will not result from the use of the insert.

The ocular medicinal inserts can also contain plasticizers, buffering agents and preservatives. Plasticizers suitable for this purpose must, of course, also be completely soluble in the lacrimal fluids of the eye. Examples of suitable plasticizers that might be mentioned are water, polyethylene glycol, propylene glycol, glycerine, trimethylol propane, di and tripropylene glycol, hydroxypropyl sucrose and the like. Typically, such plasticizers can be present in the ophthalmic insert in an amount ranging from up to 1 about 30% by weight. A particularly preferred plasticizer is water which is present in amounts of at least about 5% up to about 40%. In actual practice, a water content of from about 10% to about 20% is preferred since it may be easily accomplished and adds the desired softness and pliability to the insert.

When plasticizing the solid medicinal product with water, the product is contacted with air having a relative humidity of at least 40% until said product picks up at least about 5% water and becomes softer and more pliable. In a preferred embodiment, the relative humidity of the air is from about 60% to about 99% and the contacting is continued until the water is present in the product in amounts of from about 10% to about 20%.

Suitable water soluble preservatives which may be employed in the insert are sodium bisulfate, sodium thiosulfate, ascorbate, benzalkonium chloride, chlorobutanol, thimerosal, phenylmercuric acetate, phenylmercuric borate, parabens, benzyl alcohol and phenylethanol. These agents may be present in amounts of from 0.001 to 5% by weight of solid insert, and preferably 0.1 to 2%.

Suitable water soluble buffering agents are alkali, alkali earth carbonates, phosphates, bicarbonates, citrates, borates and the like, such as sodium phosphate, citrate, borate, acetate, bicarbonate and carbonate. These agents may be present in amounts sufficient to obtain a pH of the system of between 5.5 to 8.0 and especially 7-8; usually up to about 2% by weight of polymer. The insert may contain from about 1 mg. to 100 mg. of water soluble polymer, more particularly from 5 to 50 mg. and especially from 5 to 20 mg. The medicament is present from about 0.1 to about 25% by weight of insert.

The ability of the Formula I compound to lower intraocular pressure is determined in rabbits with experimental glaucoma induced by intraocular injection of α-chymotrypsin. Compounds of Formula I are effective in lowering intraocular pressure after topical application. Pressure is reduced in the normal and the glaucomatous eye.

The compounds (Formula I) of the present invention have $\beta$-adrenergic blocking activity. This $\beta$-adrenergic blocking activity is determined by measuring the ability of representative compounds to block the $\beta$-adrenergic stimulant effect of isoproterenol in a test animal.

The compounds of the present invention also have α-adrenergic blocking activity. This α-adrenergic blocking activity is determined, (a) in vitro by measuring the ability of a representative Formula I compound to displace radio labeled α-adrenergic antagonist from a tissue substrate or (b) in vivo, by measuring the ability of a representative Formula I compound to block the α-adrenergic stimulant effect of phenylephrine in anesthetized normotensive animals.

The present compounds exhibit antihypertensive activity of immediate onset. This rapid onset antihypertensive activity is determined by administering a representative compound of the present invention to spontaneously hypertensive (SH) rats and measuring the effect on blood pressure.

The α- and $\beta$-adrenergic blocking activity of the present compounds indicates that the compounds may be useful in humans for treating cardiovascular conditions susceptible to $\beta$-blockade therapy (e.g., angina pectoris, arrhythmia) while minimizing bronchoconstriction via α-adrenergic blockade. This $\alpha/\beta$-blocking effect can be useful in treating hypertension caused by pheochromocytoma.

For use as $\alpha/\beta$-adrenergic blocking agents, and/or antihypertensive agents the compounds of the present invention can be administered orally, by inhalation, by suppository or parenterally, i.e., intravenously, intraperitoneally, etc. and in any suitable dosage form. The compounds may be offered in a form (1) for oral administration, e.g., as tablets in combination with other compounding ingredients (diluents or carriers) customarily used such as talc, vegetable oils, polyols, benzyl alcohols, starches, gelatin and the like—or dissolved, dispersed or emulsified in a suitable liquid carrier—or in capsules or encapsulated in a suitable encapsulating material, or (2) for parenteral administration, dissolved, dispersed, or emulsified in a suitable liquid carrier or diluent or (3) as an aerosol or (4) as a suppository. The ratio of active ingredient (present compound) to compounding ingredients will vary as the dosage form required. Conventional procedures are used to prepare the pharmaceutical formulations. The effective daily dosage level for the present compounds for applications other than treatment of the eye may be varied from about 10 mg. to about 3000 mg. Daily doses ranging from about 100 to about 2500 mg. are preferred, with about 200 to about 1000 mg. being a more preferred range. Oral administration is preferred. Either single or multiple daily doses may be administered depending on unit dosage.

Compounds of formula I also have bronchodilator activity. This is determined by measuring the effectiveness of the compound to antagonize slow reacting substance of anaphylaxis (SRS-A). The compounds are thus useful to treat conditions in mammals especially human beings which benefit from bronchodilatation such as asthma, ect. For use as a bronchodilator, the compound is administered orally or parenterally in conventional dosage form such as tablet, capsule, solution, dispersion, emulsion and the like. The compound may also be administered as a spray or an aerosol using an appropriate delivery device and formulation. The oral route is preferred. Sufficient formula I compound is administered to produce the desired level of bronchodilation. Daily dosages for oral or parenteral administration may range from about 1 mg. to about 300 mg, and preferably from about 2 to about 150 mg. Spray or aerosol delivery will be in metered doses ranging from about 50 to about 1000 mcg, administered as needed.

Thus, other embodiments of the present invention are the pharmaceutical compositions containing a therapeutically effective amount of the Formula I compound and methods for (1) treating hypertension, other cardiovascular conditions, or glaucoma, (2) for lowering intraocular pressure, or (3) for effecting bronchodilation.

Compounds of formula I may be prepared by any convenient process. One such useful process is illustrated by the following set of reaction equations:

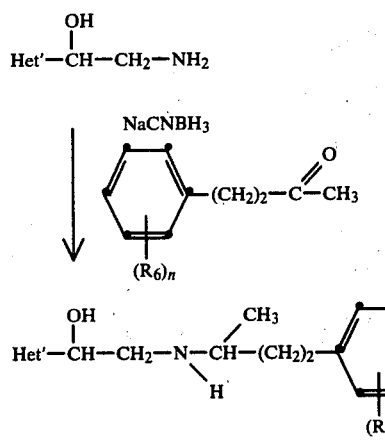

Het' is a heterocyclic group (a), (b), (c) or a suitable precursor thereof.

Another process for preparing some compounds of formula I is illustrated by the following set of reaction equations:

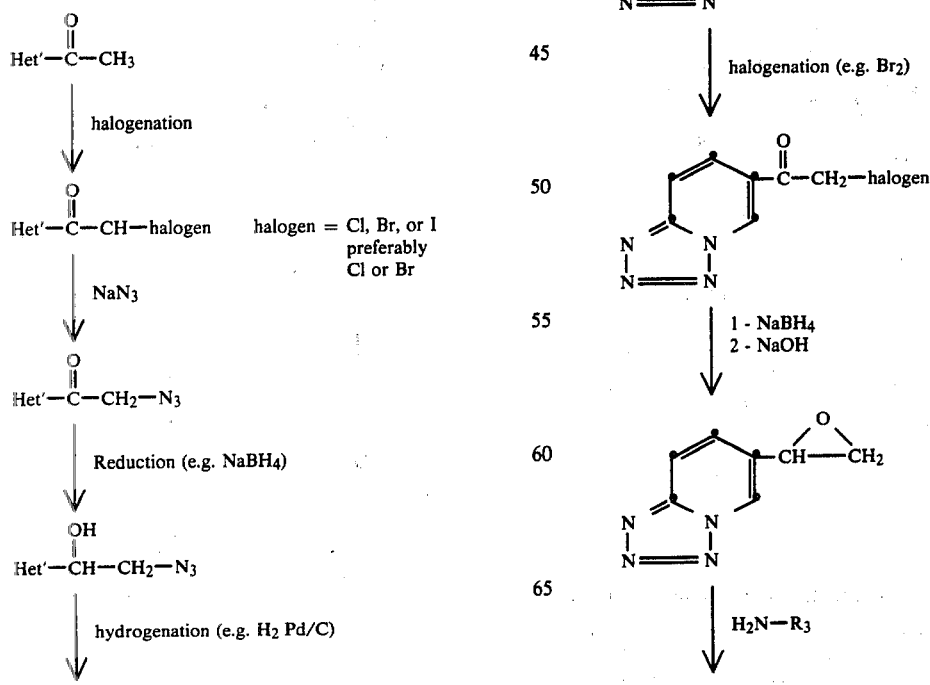

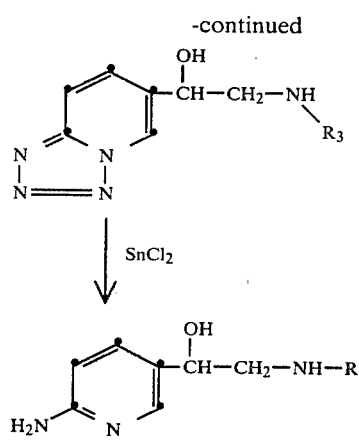
The N-oxide of the formula II compound is prepared as illustrated by the following set of reaction equations:
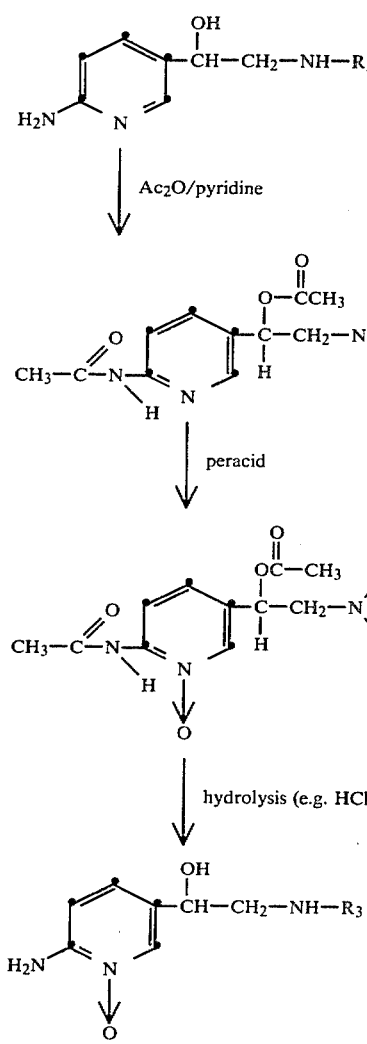
Another process for preparing some compounds of formula I is illustrated by the following set of reaction equations:
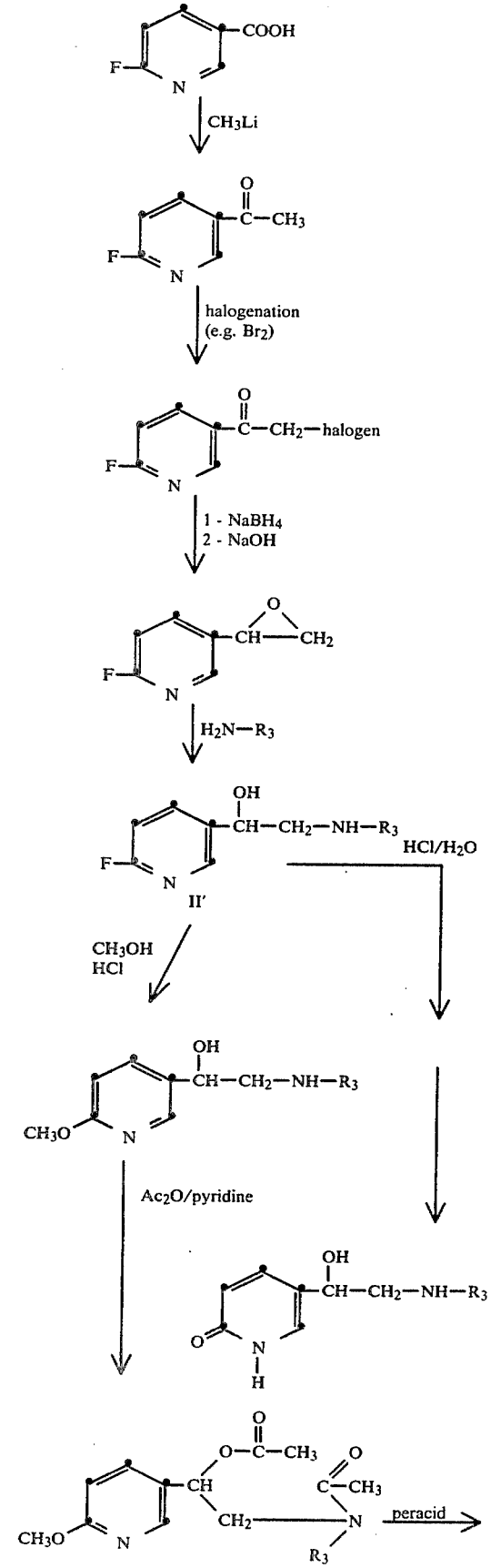

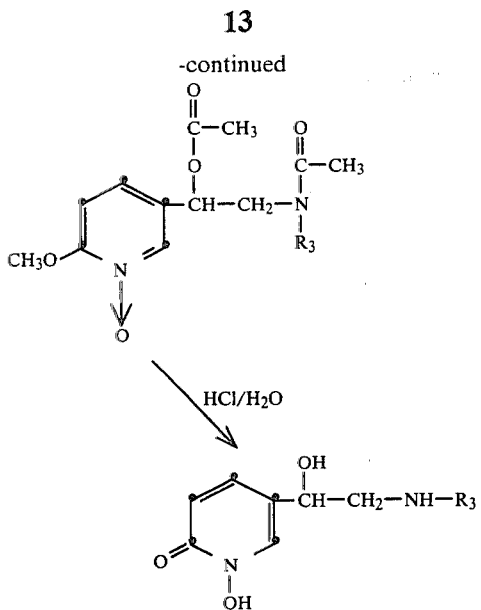

↓ HCl/H₂O

The following examples illustrate preparation of representative compounds of formula I. The processes used are those set out in the sets of equations set out above. All temperatures are in degrees Celsius.

EXAMPLE 1

Preparation of 7-[1-hydroxy-2-(4-phenyl-2-butylamino)ethyl]-2H-1,4-benzoxazin-3(4H)-one maleate salt of the formula:

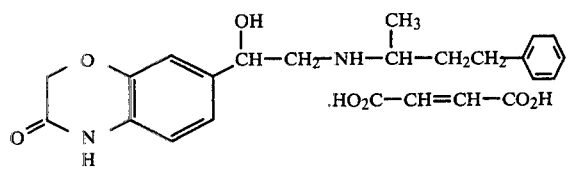

A. 7-Acetyl-2H-1,4-benzoxazin-3(4H)-one (A)

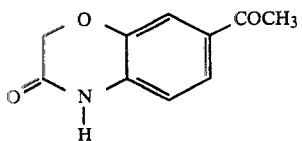

To a stirred mixture of 17.7 gm. (0.117 moles) of 4-amino-3-hydroxyacetophenone (Eur. J. Med. Chem., 9, 491 (1974)) and 35.4 gm. (0.42 moles) of NaHCO₃ in a mixture of 350 ml. of water and 350 ml. of 2-butanone was added 14 ml. (0.176 moles) of chloroacetyl chloride over 30 min. at 25° C. The reaction mixture was then stirred and heated at 90° C. for 5 hours, after which a further 1 ml. (0.013 moles) of chloroacetyl chloride was added and heating continued for 2 hours. TLC indicated no starting material remained. The reaction mixture was cooled and poured into 1500 ml. of water. After stirring for 1 hour, the precipitate was filtered and air dried to yield 16.3 gm. of A, m.p. 197°–198°. Extraction of the aqueous with ethyl acetate yielded a further 4.5 gm. of A; total yield, 93%.

B. 7-Bromoacetyl-2H-1,4-benzoxazin-3 (4H)-one (B)

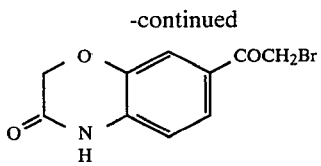

A mixture 4 gm. (20.9 mmoles) of 7-acetyl-2H-1,4-benzoxazin-3(4H)-one and 8.9 gm. (39.9 mmoles) of finely ground cupric bromide in 1000 ml. of ethyl acetate was stirred and refluxed for 18 hours. A further 3.6 gm. (16 mmoles) of cupric bromide was added and reflux continued for 6 hours. The reaction mixture was filtered, decolorized with charcoal and upon concentration there was obtained 3.8 gm. (68% yield) of B, m.p. 217°–219° C. (dec.)

C. 7-Azidoacetyl-2H-1,4-benzoxazin-3 (4H)-one (C)

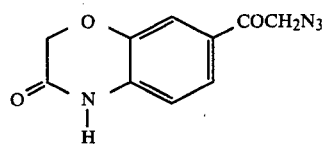

to a suspension of 270 mg. (1 mmole) of 7-bromoacetyl-2H-1,4-benzoxazin-3(4H)-one in 20 ml. of methanol was added a solution of 78 mg. (1.2 mmoles) of sodium azide in 2 ml. of water adjusted to pH 5 with acetic acid. After stirring for 20 hours at 25° C., the precipitate was filtered off, rinsed with water and air dried to give 137 mg. (59% yield) of C, m.p. 180° C. (dec.)

D. 7-(1-hydroxy-2-azidoethyl)-2H-1,4-benzoxazin-3 (4H)-one (D)

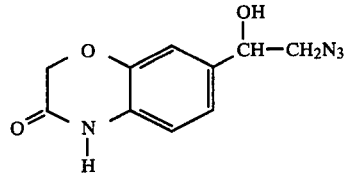

To solution of 5.6 gm. (24.1 mmoles) of 7-azidoacetyl-2H-1,4-benzoxazin-3(4H)-one in 750 ml. of methanol at 50° C. was added 4.56 gm. (120 mmoles) of sodium borohydride was added in portions (vigorous gas evolution). After addition was complete, the reaction was stirred for 1 hour, 50 ml. of water and 1.5 ml. of acetic added and the mixture evaporated to dryness. Three one hundred millilter portions of methanol were evaporated from the residue, which was then treated with 200 ml. of water. After adjusting of the pH to 5 with acetic acid, the aqueous suspension was extracted with 3×200 ml. of ethyl acetate. The combined organic extracts were washed with 0.5 N acetic acid, 5% NaHCO₃, dried (Na₂SO₄) and evaporated. Trituration of the residue with 50 ml. of ether and filtration gave 4.5 gm. (80% yield of D, m.p. 121°–123° C. (dec.)

E. 7-(1-hydroxy-2-aminoethyl)-2H-1,4-benzoxazin-3 (4H)-one hydrochloride

-continued

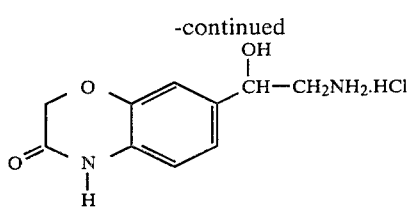
E

A solution of 4.5 gm. (19.2 mmoles) of D in 120 ml. of methanol containing 1 ml. of 12 N HCl was hydrogenated over 10% Pd/C in a Parr apparatus at 25° C. and 50 p.s.i. for 18 hours. Filtration and evaporation left 4.5 gm. of crude E, which was combined with the crude product from a second hydrogenation of 5.0 gm. of D to give 10.2 gm. of crude E. The free base of E was obtained by passage of an aqueous solution (100 ml.) of crude E through 130 ml. of AG-50W-X8 cation exchange resin (100–200 mesh) in the acid form, followed by elution with 1.5 N NH4OH. Evaporation yielded 5.2 gm. of crude E as the free base, which upon crystallization from 300 ml. of ethanol gave 3.62 gm. containing one-fourth of a mole of water: m.p. 179°–182° C.

| Anal. | C | H | N |
|---|---|---|---|
| Calc. | 56.47 | 5.88 | 13.18 |
| Found | 56.26 | 5.83 | 13.17 |

The hydrochloride (E) was prepared in ethanol and after two recrystallizations had m.p. 228° C. (dec.).

| Anal. | C | H | N | Cl |
|---|---|---|---|---|
| Calc. | 49.09 | 5.35 | 11.45 | 14.49 |
| Found | 49.19 | 5.63 | 11.32 | 14.31 |

F. 7-[1-hydroxy-2-(4-phenyl-2-butylamine)ethyl]-2H-1,4-benzoxazin-3(4H)-one maleate salt (F)

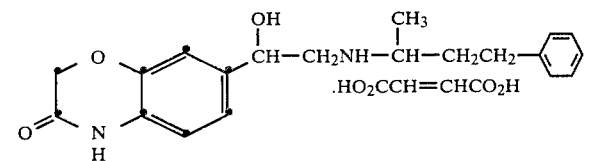

To a solution of 2.3 gm. (11 mmoles) of E free base and 1.5 gm. (6 mmoles) of E in 100 ml. of methanol were added 2.5 gm. (17 mmoles) of 4-phenyl-2-butanone and 1.07 gm. (17 mmoles) of sodium cyanoborohydride and the mixture stirred in the presence of 4A molecular sieves at 25° C. for 18 hours. TLC showed no starting materials present and one principal new product. The reaction mixture was acidified with 12 N HCl, stirred for 20 min., filtered, and evaporated and the residue slurried with ether. The insoluble hygroscopic solid was separated by filtration, suspended in 100 ml. of 1N NaHCO3, and the mixture extracted with 3×100 ml. of ethyl acetate. The combined organic extracts were washed with water, dried and evaporated to leave 4.2 gm. of solid crude F free base. This was slurried four times with 20 ml. of ether to give 2.85 gm. of purified free base. To a hot solution of the free base in ethyl acetate was added a hot solution of 0.97 gm. (8.38 mmoles) of maleic acid in a minimum of ethyl acetate (total volume was 200 ml). Upon seeding and cooling, there was obtained 3.6 gm. of crude F. This was recrystallized from 250 ml. of hot acetonitrile by addition of ether to turbidity and cooling to give 2.6 gm. (5.7 mmoles, 34% yield) of F, m.p. 132°–137° C.

| Anal. | C | H | N |
|---|---|---|---|
| Calc. | 63.14 | 6.18 | 6.14 |
| Found | 63.33 | 6.32 | 6.13 |

EXAMPLE 2

Preparation of 6-[1-hydroxy-2-(4-phenyl-2-butylamino)ethyl]-2H-1,4-benzoxazin-3(4H)-one maleate salt of the formula:

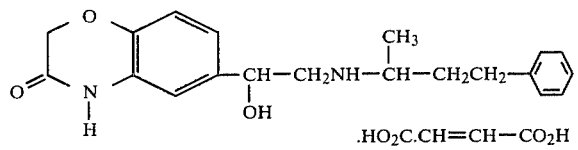

Starting with 6-chloroacetyl-2H-1,4-benzoxazin-3(4H)-one, (C.R. Acad. Sci., C, 270, 1601 (1970)), and following essentially the procedures of EXAMPLE I, steps C, D, E and F there were obtained successively:

A 6-Azidoacetyl-2H-1,4-benzoxazin-3 (4H)-one:

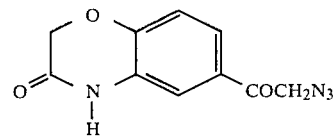

m.p. 177°–178° C. (dec.) 85% yield:

| Anal. | C | H | N |
|---|---|---|---|
| Calc. | 51.72 | 3.47 | 24.13 |
| Found | 51.55 | 3.48 | 23.90 |

B 6-(1-hydroxy-2-azidoethyl)-2H-1,4-benzoxazin-3 (4H)-one:

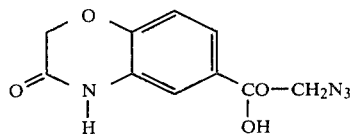

m.p. 137°–138° C., 79% yield.

| Anal. | C | H | N |
|---|---|---|---|
| Calc. | 51.28 | 4.30 | 23.92 |
| Found | 51.37 | 4.35 | 24.07 |

C 6-(1-hydroxy-2-aminoethyl)-2H-1,4-benzoxazin-3 (4H)-one:

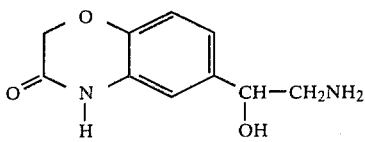

m.p. 175°–178° C., 78% yield.

| Anal. | C | H | N |
|---|---|---|---|
| Calc. | 57.68 | 5.81 | 13.46 |
| Found | 57.50 | 5.91 | 13.30 |

D 6-[1-hydroxy-2-(4-phenyl-2-butylamino)ethyl]-2H-1,4-benzoxazin-3 (4)-one maleate salt

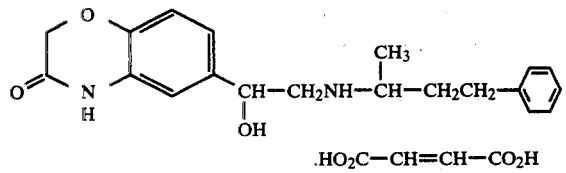

Free base: m.p. 125°–130° C., 83% yield.

| Anal. | C | H | N |
|---|---|---|---|
| Calc. | 70.56 | 7.11 | 8.23 |
| Found | 70.57 | 7.40 | 8.33 |

Maleate: m.p. 154°–157° C., 96% yield.

| Anal. | C | H | N |
|---|---|---|---|
| Calc. | 63.14 | 6.18 | 6.14 |
| Found | 63.25 | 6.19 | 6.20 |

EXAMPLE 3

Preparation of 2,3-dihydro-α-{[(1-methyl-3-phenylpropyl)amino] methyl)}-2-oxo-6-benzoxazolemethanol maleate salt of the formula:

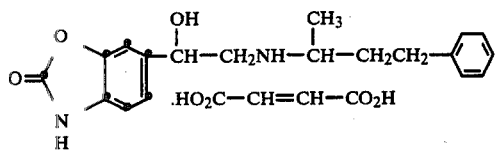

Starting with 6-chloroacetyl-2,3-dihydro-2-oxobenzoxazole (Eur. J. Med. Chem., 9, 491 (1974), and following essentially the procedures of Example 1, steps C, D, E and F, there were obtained successively:

A. 6-Azidoacetyl-2,3-dihydro-2-oxobenzoxazole:

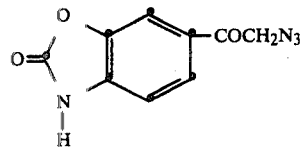

m.p. 250° C. (dec.), 78% yield.

| Anal. | C | H | N |
|---|---|---|---|
| Calc. | 49.55 | 2.77 | 25.68 |
| Found | 49.71 | 2.90 | 24.14 |

B 2,3-Dihydro-α-(azidomethyl)-2-oxo-6-benzoxazole-methanol:

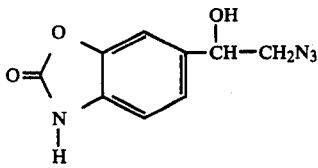

m.p. 119°–121.5° C., 78% yield.

| Anal. | C | H | N |
|---|---|---|---|
| Calc. | 49.09 | 3.66 | 25.44 |
| Found | 49.01 | 3.76 | 23.47 |

C 2,3-dihydro-α-(aminomethyl)-2-oxo-6-benzoxazole-methanol.HCl

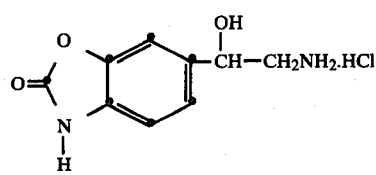

m.p. 315° C., (dec.) 60% yield.

| Anal. | C | H | N | Cl |
|---|---|---|---|---|
| Calc. | 46.86 | 4.81 | 12.14 | 15.37 |
| Found | 47.10 | 4.89 | 11.75 | 15.15 |

D 2,3-Dihydro-α-{[(1-methyl-3-phenylpropyl)amino] methyl}-2-oxo-6-benzoxazolemethanol maleate salt

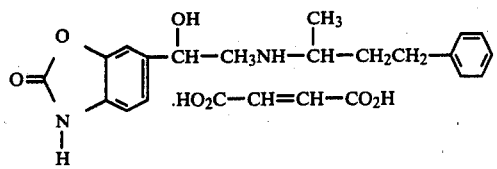

m.p. 163°–165° C., 31% yield.

| Anal. | C | H | N |
|---|---|---|---|
| Calc. | 62.43 | 5.92 | 6.33 |
| Found | 62.75 | 6.03 | 6.34 |

EXAMPLE 4

Preparation of 6-amino-α-{[(1-methyl-3-phenylpropyl)amino] methyl]}-3-pyridinemethanol dihydrochloride salt of formula:

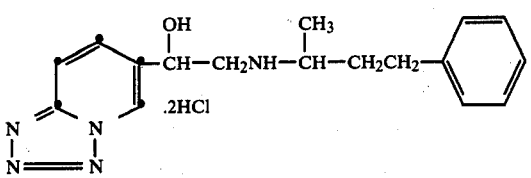

A. 6-Acetyl tetrazolo[1,5-a] pyridine (A)

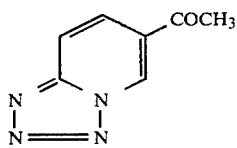

To a stirred solution of 8.4 gm. (51.6 mmoles) of 2-chloro-5-acetylpyridine and 8.4 gm. (129 mmoles) of sodium azide in 150 ml. of ethanol and 150 ml. of water was added 75 ml. of 10% HCl over a period of 20 min. The reaction mixture was then heated to reflux for 18 hours, cooled in an ice bath and the resulting crystals filtered off to give a first crop of 6.0 gm. A second crop of 1.0 gm. was obtained for a total of 7.0 gm. of A, (84.% yield), m.p. 159°–160° C.

| Anal. | C | H | N |
|---|---|---|---|
| Calc. | 51.85 | 3.73 | 34.56 |
| Found | 52.01 | 3.91 | 34.40 |

B. 6-Bromoacetyltetrazolo[1,5-a] pyridine (B)

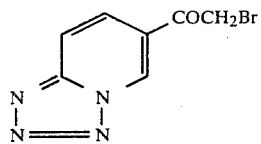

To a partial solution of 55.4 gm. (0.34 moles) of A in 1500 ml. of glacial acetic acid, saturated with HBr, and cooled in an ice bath was added a solution of 57 gm. (0.32 moles) of bromine in 500 ml. of glacial acetic acid over a period of 2 hours. The reaction was evaporated to dryness and the residue taken up in ethyl acetate. A small amount of insoluble material was filtered off and the ethyl acetate was washed with water, 1N NaHCO$_3$ solution and dried (Na$_2$SO$_4$). Evaporation left 82.4 gm. of crude product which contained 80% of B. A portion (71 gm.) of the crude material was slurried twice with 500 ml. of 10% ethyl acetate in ether to give 56 gm. of B, sufficiently pure for further use (79% yield). A sample recrystallized from ethanol had m.p. 110°–113° C.

| Anal. | C | H | N | Br |
|---|---|---|---|---|
| Calc. | 34.88 | 2.09 | 23.24 | 33.15 |
| Found | 35.05 | 2.12 | 23.14 | 33.36 |

C 2-(tetrazolo[1,5-a] pyrid-6-yl)oxirane (C)

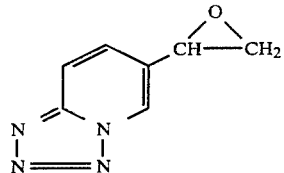

To a suspension of 37 gm. (154 mmoles) of B in 280 ml. of methanol was added 1.85 gm. (49 mmoles) of sodium borohydride with stirring at 20° C. over a period of 30 min. The reaction mixture was evaporated to dryness and agitated well with a mixture of 500 ml. of ethyl acetate and 500 ml. of 1 N NaOH. The organic layer was separated, washed with water, decolorized with charcoal, dried and evaporated to leave an oily solid. This was chromatographed over silica gel using ethyl acetate. The partially purified material thus obtained was crystallized from 130 ml. of ethanol to give 18.2 gm. (73% yield), of C, m.p. 108°–110° C.

| Anal. | C | H | N |
|---|---|---|---|
| Calc. | 51.85 | 3.75 | 34.56 |
| Found | 51.71 | 3.53 | 34.34 |

D α[(1-methyl-3-phenylpropyl)amino]methyl-6-tetrazolo[1,5-a]pyridinemethanol (D)

A solution 10 gm. (61.7 mmoles) of C and 10 gm. (67.1 mmoles) of 4-phenyl-2-aminobutane in 50 ml. of ethanol was heated to reflux for 1.5 hours. The reaction mixture was evaporated and the residue crystallized first from a minimum of ethyl acetate and recrystallized from 100 ml. of ethanol to give 11.4 gm. of D. A second crop 2.3 gm. obtained by chromatography of the mother liquors to give a total of 13.7 gm. (71% yield) of D, m.p. 117°–120° C.

| Anal. | C | H | N |
|---|---|---|---|
| Calc. | 65.57 | 6.80 | 22.48 |
| Found | 65.57 | 6.95 | 22.48 |

The maleate salt was prepared in ethylacetate: m.p. 121°–124° C.

| Anal. | C | H | N |
|---|---|---|---|
| Calc. | 59.00 | 5.90 | 16.39 |
| Found | 59.29 | 6.13 | 16.31 |

E 6-Amino-α-[(1-methyl-3-phenylpropyl)amino]methyl-3-pyridinemethanol dihydrochloride (E)

A solution of 11 gm. (35.4 mmoles) of D and 24 gm. (106 mmoles) of stannous chloride dihydrate in 60 ml. of 12 N HCl is heated to reflux for 2 hours. The reaction was evaporated to dryness, the residue suspended in 150 ml. of methanol and basified with conc. NH$_4$OH. The precipitated salts were removed by filtration and the product in the filtrate chromatographed over 600 gm. of silica gel, eluting with a mixture of CH$_2$Cl$_2$:CH$_3$OH:- conc. NH4OH (15:5:4), to give, upon evaporation of the eluate, 6.8 gm. (67% yield) of the free base of E.

The dihydrochloride salt was prepared from the free base in ethanol, by addition of 12 N HCl and cooling, in 65% yield.

m.p. 156°–158° C.

| Anal. | C | H | N | Cl |
|---|---|---|---|---|
| Calc. | 56.98 | 7.03 | 11.73 | 19.79 |
| Found | 56.58 | 7.32 | 11.29 | 19.96 |

The product E is a racemic mixture of diastereomers containing the 4 isomers S,S; S,R; R,S and R,R. By using a specific isomer of the amine reactant in step D., for example, S-4-phenyl-2-aminobutane, a mixture of 2 isomers of E i.e. S,S-E free base and R,S-E free base, is obtained. This mixture is conventionally separated, for example, by chromatography, and the individual isomers i.e. S,S-E free base and R,S-E free base, are obtained. When R-4-phenyl-2-aminobutane is used, the corresponding S,R and R,R isomers of E free base are obtained. This procedure for preparing individual isomers may be used for the preparation of any Formula I compound which involves the reaction of an epoxide and an amine.

EXAMPLE 5

Preparation of 6-amino-α-{[(1,1-dimethyl-3-phenylpropyl)amino]-methyl}-3-pyridinemethanol dihydrochloride hemihydrate:

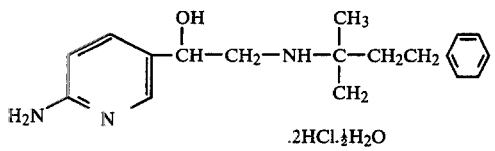

Starting with 4-phenyl-2-amino-2-methylbutane and the product C of Example IV, and following essentially the procedure of Example IV, steps D and E, there was obtained successively:

A. α-{[(1,1-dimethyl-3-phenylpropyl)amino]methyl}-6-tetrazolo[1,5-a]-pyridinemethanol (A)

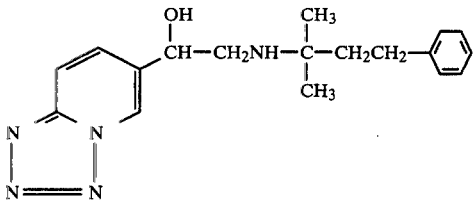

m.p. 126°–127° C., 76% yield.

| Anal. | C | H | N |
|---|---|---|---|
| Calc. | 66.44 | 7.12 | 21.52 |
| Found | 66.70 | 7.20 | 21.37 |

The maleate salt was prepared in ethylacetate: m.p. 167°–168° C., 98% yield.

| Anal | C | H | N |
|---|---|---|---|
| Calc. | 59.85 | 6.16 | 15.86 |

| Anal | C | H | N |
|---|---|---|---|
| Found | 59.88 | 6.35 | 15.74 |

B. 6-Amino-α-{[(1,1-dimethyl(-3-phenylpropyl)amino]methyl}-3-pyridinemethanol dihydrochloride hemihydrate

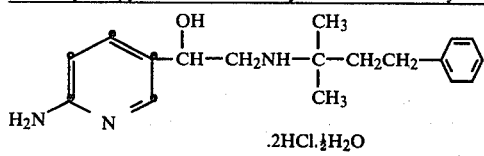

m.p. 185°–188° C. (dec.)., 54% yield.

| Anal | C | H | N | Cl |
|---|---|---|---|---|
| Calc | 56.69 | 7.14 | 11.02 | 18.60 |
| Found | 56.96 | 7.18 | 11.04 | 18.54 |

EXAMPLE 6

Preparation of 6-amino-α-{[1-methyl-3-phenylpropyl)amino]methyl}-3-pyridinemethanol-1-oxide dihydrochloride salt A

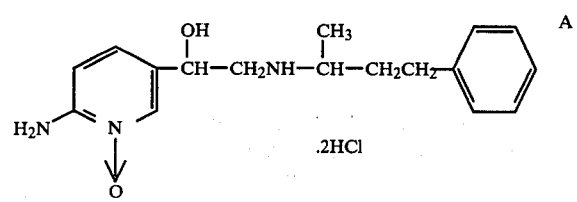

A solution of 2.0 gm. (7.02 mmoles) of the free base of the product of step E of Example 4 in a mixture of 20 ml. of pyridine and 10 ml. of acetic anhydride was stirred at 20° C. for 18 hr. The excess reactants were evaporated and the residue partitioned between 150 ml. of water and 150 ml. of ethyl acetate. The organic layer was washed with 1 N Na2CO3 solution, dried and evaporated to give 2.6 gm. (90% yield) of the triacetylated intermediate.

The protected intermediate was dissolved in 30 ml. of chloroform and 1.4 gm. (25% excess) of m-chloroperbenzoic acid was added. After stirring the solution for 3 hr. at 20° C., 2 gm. of Ca(OH)2 powder was added and stirring continued for 30 minutes. The reaction was filtered, the filtrate evaporated and the residue (2.3 gm.) was chromatographed over 400 gm. of silica gel eluting with 10% methanol in ethyl acetate. Two fractions were obtained: (a) 0.50 gm., a single diastereoisomer (b) 1.71 gm. a 1:1 mixture of diastereoisomers (2.21 gm. 82% yield).

The material from fraction (b) was dissolved in 25 ml. of 6 N HCl and heated to reflux for 3 hr., and the reaction mixture then evaporated to dryness.

The residue was dissolved in methanol, basified with conc. NH4OH, and reevaporated to dryness. The residue, containing the free base, was chromatographed over 100 gm. of silica gel using methanol-methylene chloride-conc. NH4OH (20:80:3) as eluant. The fractions containing the desired product were combined and treated with HCl in 10 ml. of ethanol. Evaporation and trituration of the residue with ether gave 1.0 gm. (67% yield) of A.

m.p. 203°–210° C. (dec), 49% overall yield.

| Anal. | C | H | N | Cl |
|---|---|---|---|---|
| Calc. | 54.56 | 6.73 | 11.23 | 18.95 |
| Found | 54.46 | 6.93 | 11.10 | 18.95 |

EXAMPLE 7

Preparation of 5-{[1-hydroxy-2-[1]-methyl-3-phenyl-propyl)amino]ethyl}-2(1H)-pyridinone fumarate hydrate.

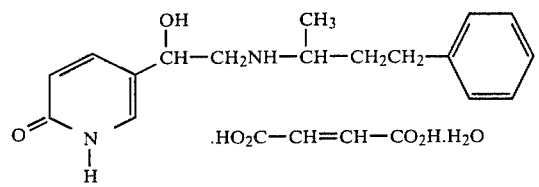

A. 5-Acetyl-2-fluoropyridine (A.)

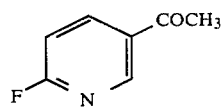

To suspension of 20 gm. (42 mmoles) of 2-fluoro-5-pyridinecarboxylic acid (J. Am. Chem. Soc., 71, 1125 (1949)) in 750 ml. of ether, stirred and cooled in ice, was added 225 ml. of 1.6 M methyl lithium (360 mmoles) in ether over 1 hr. The reaction was stirred for an additional 2 hr., then 300 ml. of ice water was added. The aqueous layer was washed with 2×100 ml. fresh ether, acidified and extracted with ether to give 5.0 gm. (25%) of unreacted starting acid.

The original ether solution was rinsed with water, dried and evaporated to yield 12.2 gm. of crude crystalline A, containing about 15% of the corresponding t-alcohol. Chromatography over silica gel, eluting with 5% ethyl acetate in methylene chloride gave 7.81 gm. (52% yield) of A. A sample crystallized from hexane had m.p. 43°–44° C.

| Anal. | C | H | N | F |
|---|---|---|---|---|
| Calc. | 60.43 | 4.35 | 10.07 | 13.65 |
| Found | 60.17 | 4.33 | 9.97 | 12.96 |

B. 5-Bromoacetyl-2-fluoropyridine (B)

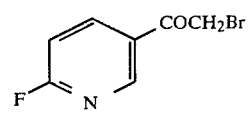

Starting with 14 gm. (100 mmoles) of A, and following the procedure described in Example 4, Step B, there was obtained 18.6 gm. of crude B, which consists of 7% of A, 82% of B and 11% of dibromoketone. This material was used without further purification for the next step.

C. (2-fluoropyrid-5-yl)oxirance (C)

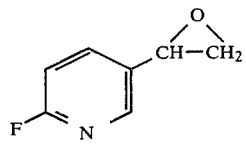

Starting with 18.6 gm. of crude B and following essentially the procedure of Example 4, Step C, there was obtained 13.4 gm. of crude C, which was suitable for use in the next step without further purification.

D. 6-Fluoro-α-{[(1-methyl-3-phenylpropyl)amino]methyl}-3-pyridinemethanol (D)

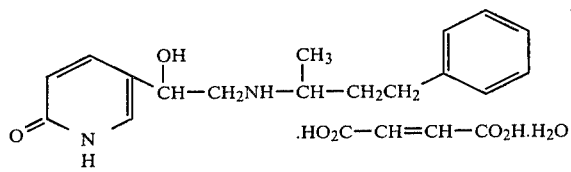

Starting with 15 gm. of crude C (containing ca. 67% of epoxide) and following essentially the procedure described in Example 4, Step D, there was obtained after chromatography, 10.04 gm. (48% yield) of D, m.p. 81°–86° C.

| Anal. | C | H | N | F |
|---|---|---|---|---|
| Calc. | 70.81 | 7.34 | 9.71 | 6.59 |
| Found | 70.61 | 7.45 | 9.69 | 6.43 |

E. 5-{1-hydroxy-2[(1-methyl-3-phenylpropyl)amino]ethyl}-2(1H)—pyridinone fumarate hydrate (E)

A solution of 2.03 gm. (7.0 mmoles) of D in 25 ml of 2 N HCl was heated to reflux for 6 hr. The reaction mixture was evaporated to dryness, re-dissolved in water and basified with NaHCO₃. The resulting mixture was evaporated to dryness, the residue exhaustively extracted with hot ethyl acetate and, after drying, the ethyl acetate was evaporated to yield 1.9 gm. of an oil (the free base of E). A sample crystallized to give m.p. 85°–89° C.

The salt was prepared by adding a solution of fumaric acid (1.4 gm) in methanol (15 ml) to the base (3.15 gm) dissolved in equal quantities of acetonitrile and methanol (250 ml. total), and evaporating the solution to about 50 ml volume. After 2 hr. there was obtained, upon filtration of the resulting crystals, 3.7 gm (75% yield) of E, m.p. 185°–189° C. (dec.)

| Anal. | C | H | N |
|---|---|---|---|
| Calc. | 59.99 | 6.71 | 6.66 |

-continued

| Anal. | C | H | N |
|---|---|---|---|
| Found | 59.49 | 6.33 | 6.41 |

EXAMPLE 8

Preparation of 5-{1-hydroxy-2-[(1,1-dimethyl-3-phenylpropyl)-amino]ethyl}-2(1H)-pyridinone dihydrochloride

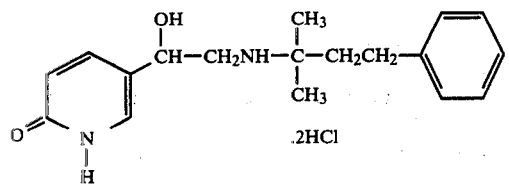

.2HCl

Starting with the epoxide C of Example 7, and reacting it with 4-phenyl-2-amino-2-methylbutane, and proceeding essentially according to Example 7, Steps D and E, there was obtained successively:

A. 6-fluoro-α-{[(1,1-dimethyl-3-phenylpropyl)amino]methyl}-3-pyridinemethanol (A)

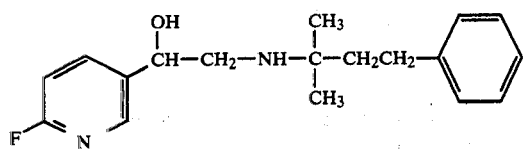

m.p. 116°–118° C., 48% yield.

| Anal. | C | H | N | F |
|---|---|---|---|---|
| Calc. | 71.50 | 7.66 | 9.26 | 6.28 |
| Found | 71.46 | 7.74 | 9.08 | 6.04 |

B. 5-{1-hydroxy-2[(1,1-dimethyl-3-phenylpropyl)amino]ethyl}-2(1H)—pyridinone dihydrochloride

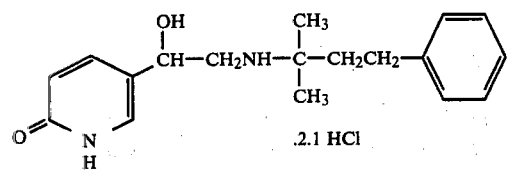

.2.1 HCl m.p. 179°–181° C., 65% yield.

| Anal. | C | H | N | Cl |
|---|---|---|---|---|
| Calc. | 57.35 | 6.97 | 7.43 | 19.74 |
| Found | 56.91 | 6.94 | 7.73 | 19.93 |

EXAMPLE 9

Preparation of 1-hydroxy-5-{(1-hydroxy-2-[(1-methyl-3-phenylpropyl)amino]ethyl}-2(1H)-pyridinone hydrochloride

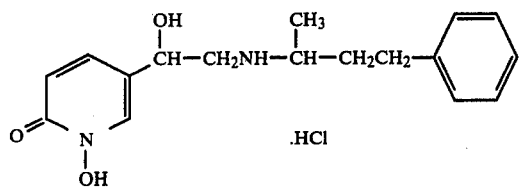

.HCl

A. 6-Methoxy-α{-{(1-methyl-3-phenylpropyl)amino]methyl}-3-pyridinemethanol (A)

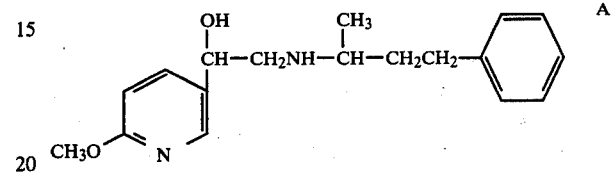

To a solution of 5.9 gm. (20.5 mmoles) of product D from Example 7 in 200 ml methanol was added 2 ml of 12 N HCl, and the reaction stirred at 20° C. It was analyzed periodically by NMR and tlc, and additional quantities of 12 N HCl were added as follows until the reaction was complete: 6 days—2 ml, 11 days, 2 ml, 17 days—reaction complete. The mixture was evaporated to dryness, partitioned between 1 N NaHCO3 and ethyl acetate, and the organic layer evaporated to give 4.8 gm (79% yield) of A, m.p. 80°–83° C., containing a small amount of the corresponding pyridone.

B. 6-Methoxy-α-{[(1-methyl-3-phenylpropyl)amino]methyl}-3-pyridinemethanol-1-oxide-O,N—diacetyl derivative (B)

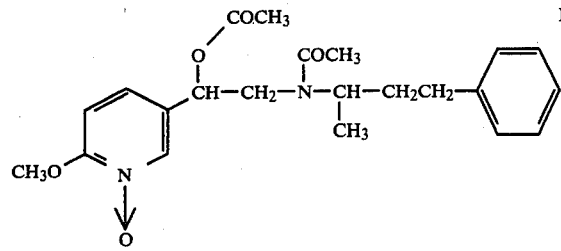

A solution of 4.6 (15.3 mmoles) of A in 250 ml of pyridine and 20 ml of acetic anhydride was stirred at 20° C. for 18 hr. The reaction mixture was then evaporated to dryness and the residue taken up in ethyl acetate, washed with 1 N NaHCO3 and water, and evaporated. The residual oil (~6.6 gm) was dissolved in 500 ml of chloroform and 6 gm (~34 mmoles) of meta-chloroperbenzoic acid was added with stirring at 20° C. After 4 days the reaction was complete and 5.3 gm of Ca(OH)2 was added to the mixture. After 30 min., the reaction was filtered and evaporated to leave 8 gm of an oil, which was chromatographed over silica gel using 10% methanol in methylene chloride as elutant. There was recovered about 2.7 gm (45%) of the unoxidized O,N-diacetyl derivative followed by 0.4 gm (6.5%) of a single isomer of B, m.p. 139°–140° C.

| Anal. | C | H | N |
|---|---|---|---|
| Calc. | 65.98 | 7.05 | 6.99 |
| Found | 66.00 | 7.18 | 7.03 |

Continued elution gave 2.1 gm (34% yield) of B as an oily mixture of diastereoisomers, used as such for the subsequent step.

C. 1-Hydroxy-5-{1-hydroxy-2-[(1-methyl-3-phenylpropyl)-amino]ethyl}-2(1H)—pyridinone hydrochloride (C)

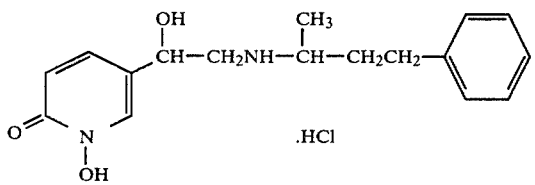

A solution of 2.6 gm (6.5 mmoles) of B in 100 ml of 2 N HCl was heated to reflux for 20 hr.; analysis by NMR showed hydrolysis and cleavage to be complete. The solution was treated with charcoal, extracted with ether, and evaporated to dryness to give a very hygroscopic solid. It was dissolved in methanol-water and neutralized with conc. NH$_4$OH. The solution of free base was absorbed onto an ion exchange column (AG50W-X8, 100–200 mesh, H+ form), and then eluted with 5% NH$_4$OH. Evaporation of the eluate 1.8 gm of crude C as the free base.

Evaporation of 1.5 gm of C free base and 0.265 gm of NH$_4$Cl dissolved in 50 ml of methanol yielded the hydrochloride salt. The residue was slurried in 25 ml of acetonitrile for 3 days, filtered and air dried to give 1.3 gm (58% yield) of C, m.p. 188° C. (dec.).

Claims to the invention follow:

What is claimed is:

1. Compounds of the formula:

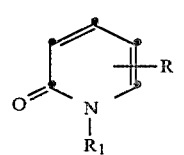 (a)

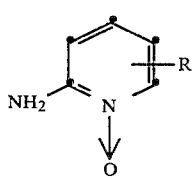 (e)

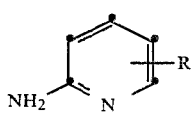 (g)

tautomers, pharmaceutically acceptable salts and individual enantiomers thereof wherein $R_1$ is H or OH,

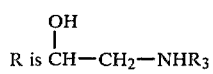

wherein

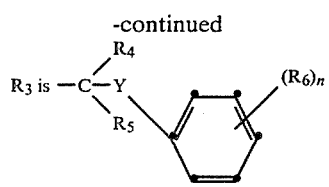

wherein $R_4$ and $R_5$ are independently selected from H and $C_1$–$C_3$ alkyl, Y is $CH_2$, $(CH_2)_2$, $(CH_2)_3$, $(CH_2)_4$ or —$CH_2$—O—

$R_6$ is H, OH, $OCH_3$, halogen, methylenedioxy or $C_1$–$C_3$ alkyl and n is 1 or 2.

2. The compounds of claim 1 formula (a) where $R_1$ is H, (e) and (g) and its tautomers.

3. The compounds of claim 2 wherein $R_6$ is H, OH or $OCH_3$.

4. The compounds of claim 3 wherein Y is $CH_2O$.

5. The compounds of claim 3 wherein Y is $CH_2$ or $(CH_2)_2$.

6. The compounds of claim 5 wherein Y is $(CH_2)_2$.

7. The compounds of claim 6 wherein $R_3$ is

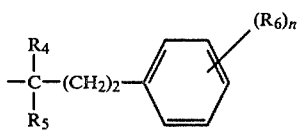

wherein $R_4$, and $R_5$, are either $CH_3$ or H.

8. The compounds of claim 7 wherein $R_4$ is H.

9. The compounds of claim 7 wherein $R_3$ is

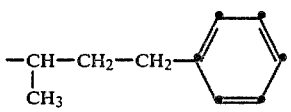

or

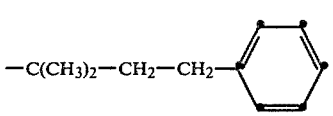

10. Compounds of claim 2 having formula (a), (e) or (g).

11. The compounds of claim 10 having formula (g).

12. The compounds of claim 10 having the formula

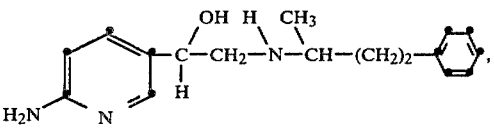

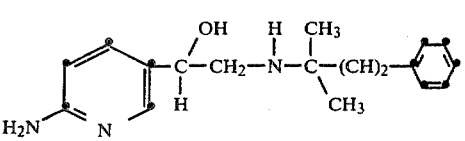

or

-continued

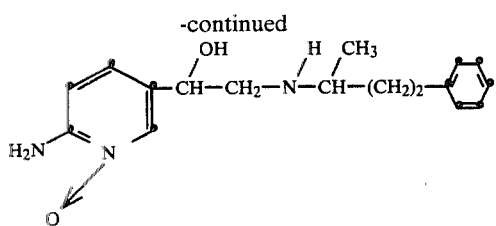

and tautomers thereof.

13. The compound of claim 12 having the formula

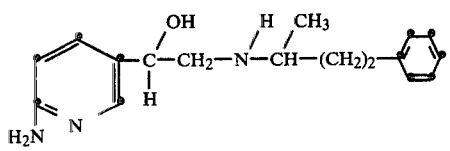

and its tautomers.

14. A compound of claim 1 having the formula:

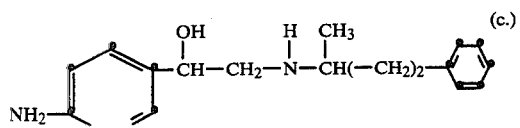 (c.)

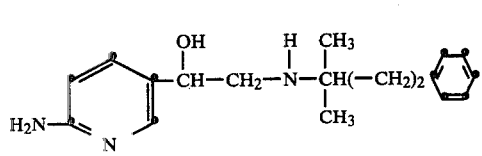 (d.)

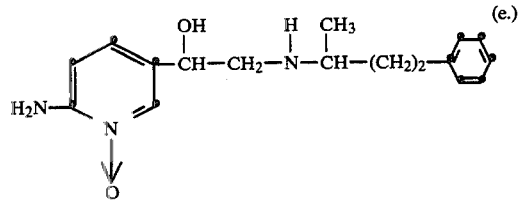 (e.)

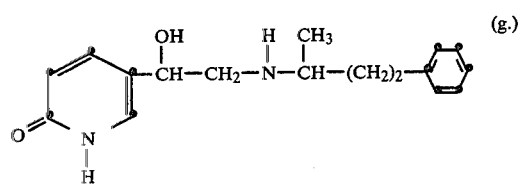 (g.)

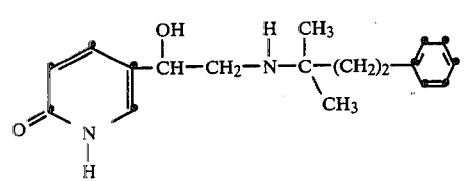 (h.)

or

-continued

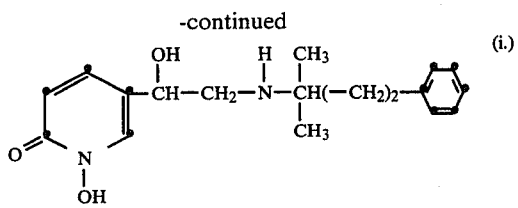 (i.)

their maleate or HCl salts, individual enantiomers and tautomers.

15. Compounds (c), (d) and (e) of claim 14.
16. Compound (c) of claim 14.
17. Compound (d) of claim 14.
18. Compound (e) of claim 14.
19. Pharmaceutical compositions for (a) reducing intraocular pressure (b) treating hypertension or (c) effecting bronchodilation containing a therapeutically effective amount of a compound of claim 1 and a carrier.
20. A method for (a) reducing intraocular eye pressure (b) treating hypertension by or (c) effecting bronchodilation by administering an effective amount of a claim 1 compound in a suitable dosage form.
21. The S,S isomer of the claim 13 compound claim.
22. The S,R isomer of the claim 13 compound.
23. The R,S isomer of the claim 13 compound.
24. The R,R isomer of the claim 13 compound.
25. Compounds of claim 1 formula (a) where $R_1$ is OH.
26. Compounds of the formula Het-CHOH-CH$_2$-NH$_2$ wherein Het has the formula

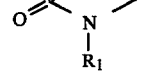 (i)

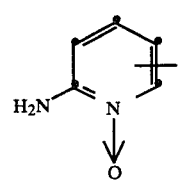 (vi)

or

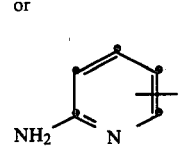 (vii)

tautomers and individual isomers thereof, where $R_1$ is H or OH.

* * * * *